United States Patent [19]

Spatz et al.

[11] 4,263,295
[45] Apr. 21, 1981

[54] PSYCHOACTIVE 3-(1-2-DIARYLETHYL)-1,4,5,6-TETRAHYDRO-1,2,4-TRIAZINES AND THEIR METHOD OF USE

[75] Inventors: David M. Spatz; Paul J. Widner, both of Midland, Mich.

[73] Assignee: The Dow Chemical Company, Midland, Mich.

[21] Appl. No.: 803,927

[22] Filed: Jun. 6, 1977

[51] Int. Cl.$^3$ .................. C07D 253/06; C07D 405/06; C07D 405/14; A61K 31/53
[52] U.S. Cl. ...................................... 424/249; 544/182
[58] Field of Search ........................ 544/182; 424/249

[56] References Cited

U.S. PATENT DOCUMENTS 3,471,485 10/1969 Trepanier .............................. 544/182
3,471,486 10/1969 Trepanier .............................. 260/248

OTHER PUBLICATIONS

Trepanier et al., *J. of Medicinal Chem.*, vol. 12, pp. 257–260 (1969).

*Primary Examiner*—John M. Ford

[57] ABSTRACT

Novel triazine compounds useful for treating central nervous system depression and anxiety in a mammal, their method of use and pharmaceutical compositions thereof.

13 Claims, No Drawings

PSYCHOACTIVE 3-(1-2-DIARYLETHYL)-1,4,5,6-TETRAHYDRO-1,2,4-TRIAZINES AND THEIR METHOD OF USE

BACKGROUND OF THE INVENTION

The compound 3-(1,2-diphenylethyl)-1,4,5,6-tetrahydro-1,2,4-triazine has been described in the literature as an antidepressant. See U.S. Pat. No. 3,471,486 and *Journal of Medicinal Chemistry*, 12, 257 (1969). This compound has been tested for antianxiety activity and found to be essentially inactive. It is surprising, therefore, to find that certain structurally related compounds exhibit both antidepressant and antianxiety activity.

SUMMARY OF THE INVENTION

The present invention is directed to novel substituted 3-(1,2-diarylethyl)-1,4,5,6-tetrahydro-1,2,4-triazines having antianxiety activity and to their method of use as psychoactive agents. The compounds of the invention are represented by the general formula

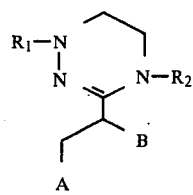

wherein A and B independently represent naphthalenyl, 1,3-benzodioxol-5-yl, phenyl, or substituted phenyl substituted with one or two moieties selected from the group consisting of lower alkyl, lower alkoxy, halo, and naphthalenyl; $R_1$ represents hydrogen or methyl; and $R_2$ represents hydrogen, methyl, or acetyl. As used herein, the terms "lower alkyl" and "lower alkoxy" refers to a moiety having from one to about three carbon atoms. The compounds of the present invention have been found to have both antidepressant and antianxiety activity when administered internally to a mammal. As used in the specification and claims, the phrase "psychoactive agent" refers to a compound having both antianxiety and antidepressant properties.

The invention also includes the pharmaceutically-acceptable salts of the substituted 3-(1,2-diarylethyl)-1,4,5,6-tetrahydro-1,2,4-triazines of the present invention. As used in the specification and claims, the phrase "pharmaceutically-acceptable salts" refers to non-toxic acid addition salts of the compounds, the anions of which are relatively innocuous to animals at dosages consistent with good psychoactive activity so that the beneficial effects of the free base are not vitiated by the side effects ascribable to the anions. Pharmaceutically-acceptable salts include those derived from mineral acids such as hydrochloric and sulfuric and from organic acids such as lactic, maleic, succinic, fumaric, glutaric, citric, malic, p-toluenesulfonic, methanesulfonic, and tartaric acid and the like.

One method for preparing the compounds of the present invention is by the reaction of a nitrile with 2-aminoethylhydrazine in the presence of a catalytic amount of a transition metal salt or elemental sulfur. The reaction is represented as follows:

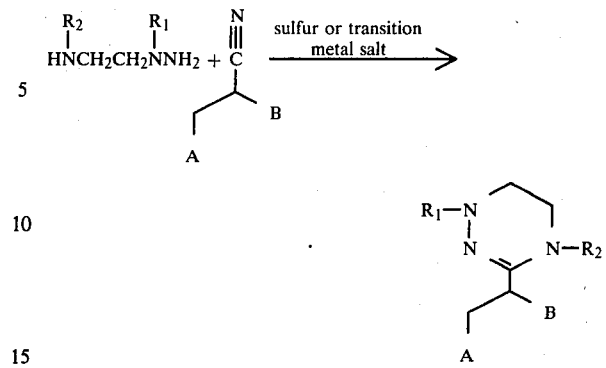

wherein A, B, $R_1$, and $R_2$ are the same as defined above. The reaction of the nitrile with 2-aminoethylhydrazine can be carried out in a suitable solvent system, usually a high boiling alcohol, but the reaction can also be carried out in the absence of solvent by simply mixing the reactants together.

The present invention also includes a method for treating anxiety in an animal, especially a mammal, by administering internally to the animal an effective antianxiety amount of one or more compounds of the present invention. As used herein, the phrase "an effective antianxiety amount" refers to the amount of the compound or compounds which is administered to the animal to alleviate central nervous system anxiety. The effective antianxiety amount depends on various known factors such as the size, type, age and condition of the animal to be treated, the particular compound or compounds of the invention employed, the route and frequency of administration, the degree of anxiety involved, the time the compound is administered relative to prior and subsequent presentation of food and liquids, etc. The phrase "an effective psychoactive amount" refers to the amount of the compound or compounds which is administered to an animal to alleviate central nervous system depression and anxiety.

DETAILED DESCRIPTION OF THE INVENTION

As noted above, the compounds of the present invention are readily prepared by the reaction of 2,3-diarylpropionitrile with 2-aminoethylhydrazine. The various 2,3-diarylpropionitrile intermediates are prepared by known procedures described in the literature. See *Synthesis*, 441–456, August 1973; *J. Org. Chem.* 36, 2948 (1971); and *Tetrahedron Letters* No. 14, pp. 1509–1511 (1966).

In practicing the method of the invention, one or more compounds of the present invention are administered internally to a mammal by a route effective to introduce an effective antianxiety amount of the compound into the blood stream of the mammal. Administration can be carried out either by a parenteral route such as by intravenous, intraperitoneal, subcutaneous or intramuscular injection, or by introduction into the gastrointestinal tract by oral administration, for example, to introduce the compound into the blood via the gastrointestinal tract. The compounds are orally effective, and generally have a higher ratio of toxic dose to effective dose when orally administered, and this route is preferred.

Generally, the active compounds are administered at a dosage rate of from about 0.2 to about 40 mg/kg of body weight with from about 0.5 to about 5 mg/kg being preferred. Higher dosage rates may be employed, for example, when the compound is administered orally in a timed release dosage form. In the case of mammals suffering from central nervous system anxiety, i.e. exhibiting symptoms of anxiety, administration of an antianxiety amount of the compound is preferably repeated at predetermined intervals. It is generally desirable to administer the individual dosages at the lowest antianxiety amount which provides the desired continuity consonant with a convenient dosing schedule.

In practicing the method of the invention, the active ingredient is preferably incorporated in a composition comprising a pharmaceutical carrier and from about 0.001 to about 95 percent by weight of the compound. The phrase "pharmaceutical carrier" refers to known pharmaceutical excipients useful in formulating pharmacologically-active compositions for internal administration to animals, and which are substantially non-toxic and non-sensitizing under conditions of use.

Suitable pharmaceutical carriers are known and disclosed in texts such as Remington's Pharmaceutical Sciences, Thirteenth Ed., Martin (Ed.) Mack Publishing Co., Easton, Pa. (1965). The compositions can be prepared by known techniques for the preparation of tablets, capsules, lozenges, troches, elixirs, syrups, emulsions, dispersions, wettable and effervescent powders, sterile injectable compositions, and can contain suitable excipients known to be useful in the preparation of the particular type of composition desired.

Dosage units adaptable to oral administration such as tablets, capsules, lozenges, elixirs, syrups and the like are preferred and the active compound can be formulated in conventional timed release capsule or tablet formulations.

Preferred compositions include sterile injectable solutions containing from about 0.001 to about 10 percent by weight of the compound in a pharmaceutical carrier suitable for injection, such as isotonic saline solution, Ringer's injection USP, and lactated Ringer's USP, and the like.

The following examples will further illustrate the present invention but are not to be construed as a limitation thereon.

EXAMPLE 1

Preparation of 3-(2-(4-fluorophenyl)-1-phenylethyl)-1,4,5,6-tetrahydro-1,2,4-triazine monohydrochloride A mixture containing 5.0 grams of 1-phenyl-2-p-fluorophenyl propionitrile and 0.5 grams of elemental sulfur was placed in a 50 ml round-bottomed flask equipped with a condenser, magnetic stirrer and maintained under a nitrogen atmosphere. A minimal amount of 2-methoxyethanol (5 ml) was added and the mixture was heated at 90° C. for 2 hours to dissolve the sulfur. To the heated solution, 3.3 grams of 2-aminoethylhydrazine was slowly injected, and the resultant blue-green reaction mass was heated at 90° C. for 18 hours. The reaction mass was quenched by the addition of 30 ml of toluene, transferred to a separatory funnel, and an additional 70 ml of toluene added.

The toluene was washed with water and saturated sodium chloride solution. The organic layer was separated, dried with sodium sulfate, and filtered. Dry hydrogen chloride gas was bubbled into the toluene solution to give the 3-(2-(4-fluorophenyl)-1-phenylethyl)-1,4,5,6-tetrahydro-1,2,4-triazine monohydrochloride as a precipitate. The crude product was dried under vacuum and recrystallized from isopropanol. The salt was found to have a melting point of 220°–222° C.

Elemental analysis showed carbon 63.95%, hydrogen 6.02%, and nitrogen 13.09% as compared to theoretical values of carbon 63.84%, hydrogen 5.79%, and nitrogen 13.14%.

Using essentially the same procedure outlined in Example 1 above a number of other 3-(1,2-diarylethyl)-1,4,5,6-tetrahydro-1,2,4-triazines were prepared having the general formula:

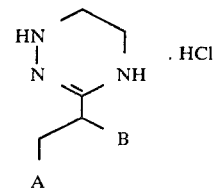

The compounds are described in Table I below.

TABLE I

| Example No. | A | B | Melting Point °C. |
|---|---|---|---|
| 2 | p-chlorophenyl | phenyl | 212–213 |
| 3 | p-fluorophenyl | p-methoxyphenyl | 145–147 |
| 4 | phenyl | p-methylphenyl | 217–219 |
| 5 | m-methylphenyl | phenyl | 184–186 |
| 6 | p-methylphenyl | phenyl | 141–143 |
| 7 | m-chlorophenyl | phenyl | 144–146 |
| 8 | phenyl | m-methylphenyl | 177–178.5 |
| 9 | phenyl | 1,3-benzodioxol-5-yl | 95–98 |
| 10 | phenyl | 2-naphthalenyl | 220–221 |
| 11 | phenyl | 1-naphthalenyl | 213–215 |
| 12 | 3,4-dimethylphenyl | phenyl | 211–213 |
| 13 | 2,6-dichlorophenyl | phenyl | 135–138 |
| 14 | 3,4-dichlorophenyl | phenyl | 224–225 |
| 15 | 1-naphthalenyl | phenyl | 248–249 |
| 16 | 2-naphthalenyl | phenyl | 219–220 |
| 17 | m-fluorophenyl | phenyl | 233–235 |

In addition to the compounds shown in Table I, two compounds were prepared having substitutions on the triazine ring. These compounds are:

EXAMPLE 18

3-(2-(4-Chlorophenyl)-1-phenylethyl)-1,4,5,6-tetrahydro-1-methyl-1,2,4-triazine monohydrochloride.

EXAMPLE 19

4-acetyl-3-(1,2-diphenylethyl)-1,4,5,6-tetrahydro-1-methyl-1,2,4-triazine monohydrochloride.

EXAMPLE 20

Compounds exhibiting antianxiety properties block the stress induced rise of serum corticosteroid levels. See *British Medical Journal,* 1971 (2), p. 310–313. Corticosteroid levels were compared between stressed male rats pretreated with 20 mg/kg of the active compound given by intraperitoneal injection to corticosteroid levels of stressed male rats pretreated with saline. Blood (3 ml) was collected by means of cardiac puncture after methoxyflurane anesthesia. Following clotting, the blood was centrifuged to separate the serum for use in the corticosteroid analysis.

The analysis was carried out by adding 5 ml of methylene chloride to 300 μl of the serum sample and vortexing the sample for 15–20 seconds. The samples were then centrifuged at 41 xg for about 5 minutes. The lipid layer was removed by aspiration and 3 ml of the methylene chloride fraction was transferred to a clean tube. To this sample, 3 ml of fluorescence reagent (25% ethanol and 75% concentrated sulfuric acid) was added and vortexed for 5 seconds. Fluorescence development was complete in 20 minutes and was read on a Perkin-Elmer® fluorometer Model 204 at an exciter wavelength of 470 mµ and an analyzer wavelength of 530 mµ. This assay measures free cortisol and corticosterone. The corticosteroid values were calculated as follows:

Corticosteriod (µg%) = $\frac{\text{fluorescence of sample} - \text{fluorescence of blank}}{\text{fluorescence of standard} - \text{fluorescence of blank}} \times 25\ \mu g\%$ Using the procedure described above, the compounds of the present invention were shown to have antianxiety activity. The results are shown in Table II below. Values below 100% are indicative of activity.

EXAMPLE 22

Groups of four mice were administered 30 mg/kg of the 3-(1,2-diarylethyl)-1,4,5,6-tetrahydro-1,2,4-triazine compounds by intraperitoneal injection via an aqueous carrier. A similar group of mice serving as controls were injected only with the carrier. After 30 minutes, both groups of mice were injected subcutaneously with 2.5 mg/kg of reserpine. The administration of reserpine to the control mice resulted in a classical progression of symptoms beginning with a drooping of the eyelids (ptosis) and later culminating in a generalized depression with decreased spontaneous motor activity and decreased responsiveness to auditary and tacticle stimuli.

Animals injected with the triazine compound were graded after 45 minutes on the following basis: no ptosis=0, partial ptosis=1, complete ptosis=2. Complete protection against reserpine-induced ptosis gives a value of 0 or 100%. The percent protection for each of the compounds is given in Table II.

TABLE II

| Compound Example Number | % Inhibition of Reserpine Ptosis | Serum Corticosteroid Levels µg % |
|---|---|---|
| 1 | 63 | 25 |
| 2 | 88 | 13 |
| 3 | 38 | 82 |
| 4 | 38 | 67 |
| 5 | 25 | 32 |
| 6 | 50 | 62 |
| 7 | 88 | 75 |
| 8 | 38 | 52 |
| 9 | 50 | 33 |
| 10 | 50 | 54 |
| 11 | 25 | 77 |
| 12 | 25 | 33 |
| 13 | 88 | 39 |
| 14 | 63 | 79 |
| 15 | 13 | 72 |
| 16 | 42 | 39 |
| 17 | 25 | 62 |
| 18 | 50 | 77 |
| 19 | 13 | 77 |
| Saline Control | 0 | 100 |

It will be seen from Table II that the compounds of Examples 1, 2, 9, 12, and 16 are especially active as antianxiety agents. The other compounds shown in the table while generally less active than the compounds of Examples 1, 2, 9, 12, and 16 also display significant activity as antianxiety agents. In addition to the antianxiety properties already noted, the following compounds were also found to be highly active as antidepressants and as such are especially preferred as psychoactive agents, i.e. agents having both antianxiety and antidepressant properties:

3-(2-(4-Chlorophenyl)-1-phenylethyl)-1,4,5,6-tetrahydro-1,2,4-triazine monohydrochloride (Example 2);

3-(2-(4-Fluorophenyl)-1-(4-methoxyphenyl)ethyl)-1,4,5,6-tetrahydro-1,2,4-triazine monohydrochloride (Example 3);

3-(1-(4-Methylphenyl)-2-phenylethyl)-1,4,5,6-tetrahydro-1,2,4-triazine monohydrochloride (Example 4);

3-(1-(2-Naphthalenyl)-2-phenylethyl)-1,4,5,6-tetrahydro-1,2,4-triazine monohydrochloride (Example 10); and 3-(2-(2,6-Dichlorophenyl)-1-phenylethyl)-1,4,5,6-tetrahydro-1,2,4-triazine monohydrochloride (Example 13).

We claim:

1. An antianxiety compound of the formula

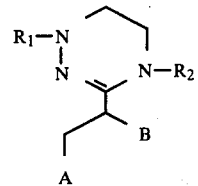

wherein A and B independently represent 1,3-benzodioxol-5-yl, phenyl, or substituted phenyl substituted with one or two moieties selected from the group consisting of lower alkyl, lower alkoxy, halo, and naphthalenyl; $R_1$ represents hydrogen or methyl; and $R_2$ represents hydrogen, methyl, or acetyl with the proviso that both A and B cannot be phenyl and further including the pharmaceutically-acceptable salts thereof.

2. The compound of claim 1 wherein $R_1$ and $R_2$ are hydrogen.

3. The compound of claim 2 which is 3-(2-(4-chlorophenyl)-1-phenylethyl)-1,4,5,6-tetrahydro-1,2,4-triazine and the pharmaceutically-acceptable salts thereof.

4. The compound of claim 2 which is 3-(2-(4-fluorophenyl)-1-(4-methoxyphenyl)ethyl)-1,4,5,6-tetrahydro-1,2,4-triazine and the pharmaceutically-acceptable salts thereof.

5. The compound of claim 2 which is 3-(1-(4-methylphenyl)-2-phenylethyl)-1,4,5,6-tetrahydro-1,2,4-triazine and the pharmaceutically-acceptable salts thereof.

6. The compound of claim 2 which is 3-(2-(2,6-dichlorophenyl)-1-phenylethyl)-1,4,5,6-tetrahydro-1,2,4-triazine and the pharmaceutically-acceptable salts thereof.

7. A method of treating anxiety in a mammal which comprises administering internally to the mammal an effective antianxiety amount of a compound of the formula

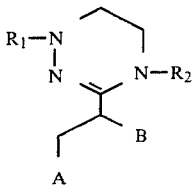

wherein A and B independently represent naphthalenyl, 1,3-benzodioxol-5-yl, phenyl, or substituted phenyl substituted with one or two moieties selected from the group consisting of lower alkyl, lower alkoxy, halo, and naphthalenyl; $R_1$ represents hydrogen or methyl; and $R_2$ represents hydrogen, methyl, or acetyl with the proviso that both A and B cannot be phenyl and further including the pharmaceutically-acceptable salts thereof.

8. The method of claim 7 wherein $R_1$ and $R_2$ of the compound are hydrogen.

9. The method of claim 8 wherein the compound is 3-(2-(4-chlorophenyl)-1-phenylethyl)-1,4,5,6-tetrahydro-1,2,4-triazine and the pharmaceutically-acceptable salts thereof.

10. The method of claim 8 wherein the compound is 3-(2-(4-fluorophenyl)-1-(4-methoxyphenyl)ethyl)-1,4,5,6-tetrahydro-1,2,4-triazine and the pharmaceutically-acceptable salts thereof.

11. The method of claim 8 wherein the compound is 3-(1-(4-methylphenyl)-2-phenylethyl)-1,4,5,6-tetrahydro-1,2,4-triazine and the pharmaceutically-acceptable salts thereof.

12. The method of claim 8 wherein the compound is 3-(1-(2-naphthalenyl)-2-phenylethyl)-1,4,5,6-tetrahydro-1,2,4-triazine and the pharmaceutically-acceptable salts thereof.

13. The method of claim 8 wherein the compound is 3-(2-(2,6-dichlorophenyl)-1-phenylethyl)-1,4,5,6-tetrahydro-1,2,4-triazine and the pharmaceutically-acceptable salts thereof.

* * * * *